US012678157B2

(12) United States Patent     (10) Patent No.:   US 12,678,157 B2

Gillespie, Jr. et al.     (45) Date of Patent:     Jul. 14, 2026

(54) HOUSING FOR STORING SUTURES THEREIN, AND METHODS OF USE THEREFOR

(71) Applicant: Origami Surgical, Inc., Madison, NJ (US)

(72) Inventors: John Gillespie, Jr., Dover, MA (US); Joshua Hubbard, New Milford, CT (US); Patrick J. Culligan, Jr., Madison, NJ (US)

(73) Assignee: Origami Surgical, Inc., Madison, NJ (US)

( * ) Notice: Subject to any disclaimer, the term of this patent is extended or adjusted under 35 U.S.C. 154(b) by 477 days.

(21) Appl. No.: 17/732,933

(22) Filed: Apr. 29, 2022

(65) Prior Publication Data

US 2022/0346778 A1     Nov. 3, 2022

Related U.S. Application Data

(60) Provisional application No. 63/181,400, filed on Apr. 29, 2021.

(51) Int. Cl.
| | |
|---|---|
| *A61B 17/04* | (2006.01) |
| *A61B 17/06* | (2006.01) |

(Continued)

(52) U.S. Cl.
CPC .. *A61B 17/06114* (2013.01); *A61B 17/06061* (2013.01); *A61B 50/30* (2016.02);
(Continued)

(58) Field of Classification Search
CPC ........ A61B 17/06114; A61B 17/06061; A61B 17/06138; A61B 17/0483; A61B 17/0469;
(Continued)

(56) References Cited

U.S. PATENT DOCUMENTS

| | | | | |
|---|---|---|---|---|
| 1,234,051 A | * | 7/1917 | Lukens | ............ A61B 17/06133 |
| | | | | 206/63.3 |
| 2,831,572 A | | 4/1958 | Messina | |

(Continued)

FOREIGN PATENT DOCUMENTS

WO     2011022401 A1     2/2011

OTHER PUBLICATIONS

International Search Report and Written Opinion of the International Searching Authority for PCT/US10/45762; pp. 1-5; Oct. 6, 2010.

*Primary Examiner* — Gideon R Weinerth
(74) *Attorney, Agent, or Firm* — FARBER LLC

(57) ABSTRACT

Various embodiments for a surgical element carrier are described. The surgical element carrier includes a housing dimensioned for insertion through a surgical port during a surgery, where the housing has a first housing portion and a second housing portion movable relative to the first housing portion between a closed position and an open position. The surgical element carrier is configured to retain surgical elements, such as sutures, in a stacked arrangement within the housing that are accessible when the surgical element carrier is in the open position. Further, the surgical element carrier further includes a spacer having a spacer body. The spacer may be positioned between at least two of the surgical elements. The spacer includes a projecting portion extending from a side of the spacer, where the projecting portion may fold over the spacer body to at least partially overlap one of the surgical elements positioned thereon.

8 Claims, 6 Drawing Sheets

(51) Int. Cl.
    *A61B 50/20*         (2016.01)
    *A61B 50/30*         (2016.01)
(52) U.S. Cl.
    CPC .............. *A61B 2017/06147* (2013.01); *A61B 2017/06152* (2013.01); *A61B 2050/3007* (2016.02); *A61B 2050/3008* (2016.02)
(58) Field of Classification Search
    CPC ......... A61B 50/30; A61B 2017/06147; A61B 2017/06152; A61B 2017/06142; A61B 2050/3007; A61B 2050/3008; A61B 17/06133; A61B 17/06066; A61B 17/06166
    USPC .............. 206/63.3; 242/613.3; 606/228, 222
    See application file for complete search history.

(56)             References Cited

U.S. PATENT DOCUMENTS

| | | | | |
|---|---|---|---|---|
| 3,162,307 A | * | 12/1964 | Regan, Jr. ........ | A61B 17/06138 206/63.3 |
| 3,206,018 A | * | 9/1965 | Lewis ................ | A61B 17/0401 206/63.3 |
| 3,227,265 A | | 1/1966 | Schneider | |
| 3,444,994 A | * | 5/1969 | Kaepernik ....... | A61B 17/06138 206/63.3 |
| 3,944,069 A | | 3/1976 | Eldridge, Jr. | |
| 4,014,434 A | * | 3/1977 | Thyen .............. | A61B 17/06138 229/87.01 |
| 4,120,397 A | | 10/1978 | Neumann | |
| 4,243,140 A | | 1/1981 | Thrun | |
| 4,254,862 A | | 3/1981 | Barratt | |
| 4,391,365 A | * | 7/1983 | Batchelor ........ | A61B 17/06138 229/92.7 |
| 4,418,821 A | | 12/1983 | Sandel | |
| 4,491,218 A | * | 1/1985 | Aday .............. | A61B 17/06138 206/388 |
| 4,596,329 A | | 6/1986 | Eldridge, Jr. | |
| 4,637,513 A | | 1/1987 | Eldrige, Jr. | |
| 4,736,844 A | | 4/1988 | Scott et al. | |
| 4,967,902 A | | 11/1990 | Sobel et al. | |
| 5,024,323 A | | 6/1991 | Bolton | |
| 5,101,968 A | * | 4/1992 | Henderson ....... | A61B 17/06138 206/227 |
| 5,145,063 A | | 9/1992 | Lee | |
| 5,228,565 A | * | 7/1993 | Sinn ................ | A61B 17/06133 53/430 |
| 5,236,083 A | * | 8/1993 | Sobel .............. | A61B 17/06133 206/227 |
| 5,249,671 A | * | 10/1993 | Sinn ................ | A61B 17/06133 206/382 |
| 5,249,673 A | * | 10/1993 | Sinn ................ | A61B 17/06133 206/382 |
| 5,277,299 A | * | 1/1994 | Holzwarth ....... | A61B 17/06138 206/476 |
| 5,344,005 A | * | 9/1994 | Kettner ........... | A61B 17/06138 206/63.3 |
| 5,348,146 A | * | 9/1994 | Sterling .......... | A61B 17/06138 206/63.3 |
| 5,350,060 A | | 9/1994 | Alpern et al. | |
| 5,366,081 A | * | 11/1994 | Kaplan ................. | A01N 37/36 206/339 |
| 5,494,154 A | * | 2/1996 | Ainsworth ....... | A61B 17/06138 206/382 |

| | | | | |
|---|---|---|---|---|
| 5,533,611 A | * | 7/1996 | Bordighon ....... | A61B 17/06138 206/388 |
| 5,538,132 A | | 7/1996 | Propp et al. | |
| 5,566,821 A | * | 10/1996 | Brown ............. | A61B 17/06138 206/388 |
| 5,582,288 A | * | 12/1996 | Zatarga ........... | A61B 17/06138 206/339 |
| 5,617,952 A | | 4/1997 | Kranendonk | |
| 5,788,062 A | * | 8/1998 | Cerwin .................. | B65B 63/06 206/380 |
| 5,799,788 A | | 9/1998 | Webb | |
| 5,871,089 A | * | 2/1999 | Odermatt ......... | A61B 17/06138 206/227 |
| 5,887,706 A | | 3/1999 | Pohle et al. | |
| 5,906,273 A | * | 5/1999 | Pohle .............. | A61B 17/06133 206/63.3 |
| 6,029,805 A | * | 2/2000 | Alpern ............ | A61B 17/06138 206/388 |
| 6,138,440 A | * | 10/2000 | Gemma ........... | A61B 17/06133 53/430 |
| 6,659,270 B2 | | 12/2003 | Williamson et al. | |
| 6,719,128 B2 | | 4/2004 | Alpern et al. | |
| 6,739,450 B2 | * | 5/2004 | Roshdy ............ | A61B 17/06138 206/227 |
| 6,986,780 B2 | * | 1/2006 | Rudnick ............ | A61B 10/0096 606/1 |
| 7,036,661 B2 | | 5/2006 | Anthony et al. | |
| 7,070,051 B2 | | 7/2006 | Kanner et al. | |
| 7,353,946 B2 | * | 4/2008 | Cervantes ........... | A61M 25/002 206/428 |
| 7,441,660 B2 | | 10/2008 | Caron | |
| 7,497,330 B2 | | 3/2009 | Anthony et al. | |
| 8,091,321 B2 | * | 1/2012 | Malinowski ..... | A61B 17/06138 53/430 |
| 8,418,851 B2 | | 4/2013 | Culligan et al. | |
| 8,746,445 B2 | * | 6/2014 | Kennedy .......... | A61B 17/06133 206/63.3 |
| 10,561,414 B2 | * | 2/2020 | Dey ................. | A61B 17/06133 |
| 10,792,037 B2 | * | 10/2020 | Jafarishad ........ | A61B 17/06133 |
| 2002/0175091 A1 | | 11/2002 | Williamson, IV .......................... A61B 17/06138 206/227 |
| 2003/0155259 A1 | | 8/2003 | Koseki | |
| 2004/0020795 A1 | * | 2/2004 | Braginsky ........ | A61B 17/06138 606/228 |
| 2004/0050721 A1 | | 3/2004 | Roby et al. | |
| 2004/0129591 A1 | | 7/2004 | Koseki | |
| 2005/0269228 A1 | | 12/2005 | Kanner et al. | |
| 2007/0055294 A1 | | 3/2007 | Giap | |
| 2007/0227914 A1 | * | 10/2007 | Cerwin ........... | A61B 17/06133 206/63.3 |
| 2008/0243141 A1 | | 10/2008 | Privitera et al. | |
| 2010/0230300 A1 | * | 9/2010 | Hunter ............. | A61B 17/06114 206/63.3 |
| 2011/0046667 A1 | * | 2/2011 | Culligan .......... | A61B 17/06161 206/370 |
| 2012/0055828 A1 | * | 3/2012 | Kennedy .......... | A61B 17/06133 206/363 |
| 2012/0123472 A1 | * | 5/2012 | Culligan .......... | A61B 17/06114 606/224 |
| 2012/0217176 A1 | * | 8/2012 | Dacey ................... | A61F 2/0095 206/204 |
| 2017/0172570 A1 | * | 6/2017 | Wentling ............. | B65D 5/4266 |
| 2020/0268383 A1 | * | 8/2020 | Vailhe ............. | A61B 17/06133 |
| 2023/0414910 A1 | * | 12/2023 | Culligan ............. | A61L 31/044 |

\* cited by examiner

THE STITCHKIT "SUTURE HOLDER BASE"

HOUSING FOR STORING SUTURES THEREIN, AND METHODS OF USE THEREFOR

CROSS-REFERENCE TO RELATED APPLICATION

This application claims priority to co-pending U.S. provisional application entitled, "Housing for Storing Sutures Therein, and Methods of Use Therefor," having Ser. No. 63/181,400, filed Apr. 29, 2021, which is entirely incorporated herein by reference.

BACKGROUND

Many surgeries are performed using robotic technology, such as the DA VINCI® surgical system commonly used for laparoscopic surgeries. Surgical element carriers have been designed to include a housing that may be inserted through a surgical port during a surgery that can be manipulated during the surgery. For instance, a clam-shell type of housing of a surgical element carrier may be sized and dimensioned to contain surgical elements therein, such as sutures. Ends of the housing are designed such that they can be manipulated by a surgeon or by a robotic manipulator.

U.S. Pat. No. 6,986,780 B2 discloses a surgical element carrier and method for use. The surgical element carrier includes a housing dimensioned to contain therein surgical elements, and dimensioned for insertion through a surgical port used in minimally invasive surgeries. The housing further includes a first housing portion and a second housing portion movable relative to the first housing portion between a closed position wherein the surgical elements are substantially surrounded by the housing, and an open position where the surgical elements are at least partially exposed and removable from the housing.

TECHNICAL FIELD

The present disclosure relates generally to the field of medical devices, and in particular, to an apparatus for housing surgical elements, such as sutures, and methods of use and manufacture therefor.

BRIEF DESCRIPTION OF THE DRAWINGS

Many aspects of the present disclosure can be better understood with reference to the following drawings. The components in the drawings are not necessarily to scale, with emphasis instead being placed upon clearly illustrating the principles of the disclosure. Moreover, in the drawings, like reference numerals designate corresponding parts throughout the several views.

DETAILED DESCRIPTION

The present disclosure may be understood more readily by reference to the following detailed description of the disclosure taken in connection with the accompanying drawing figures, which form part of this disclosure. It is also understood that the present disclosure is not limited to the specific devices, methods and conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value indicates at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 3:
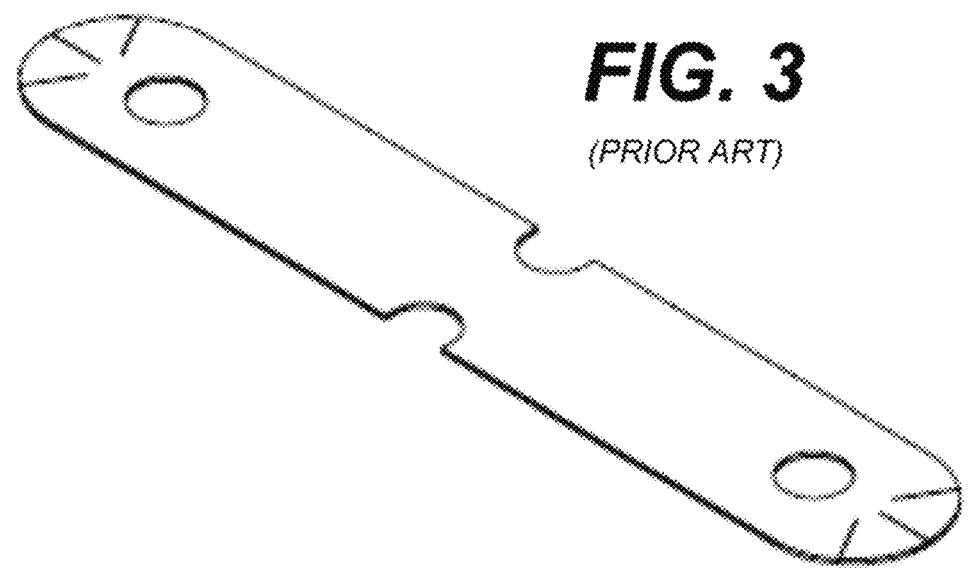
FIG. 3 is a perspective view of a spacer previously used in the apparatus of FIG. 1.
Figure 4:
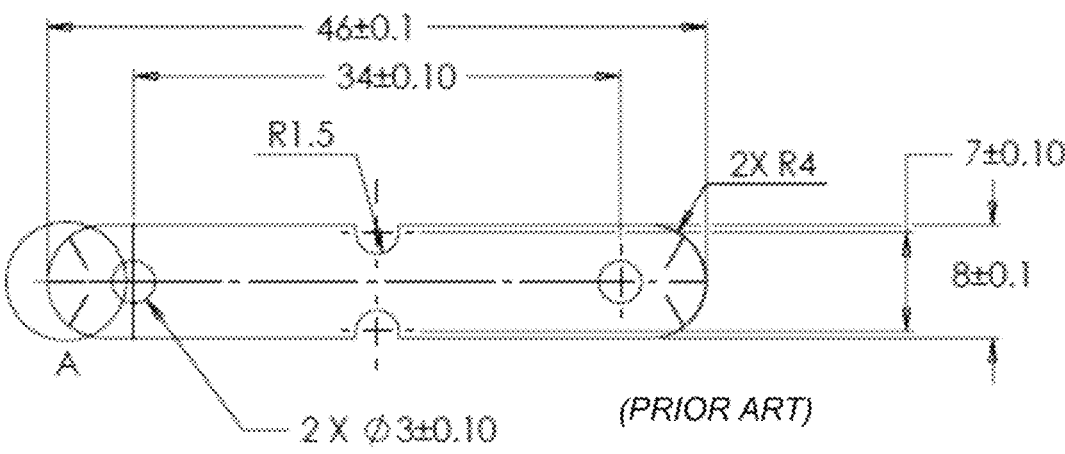
FIG. 4 is a top view of a spacer previously used in the apparatus of FIG. 1.

Today, existing surgical element carriers are only able to hold very flexible sutures as the sutures are prone to entanglement. As such, existing surgical element carriers are not able to retain barbed sutures or other sutures having non-uniform cross-sections. Otherwise, entanglement will occur prior to or during a surgical procedure. While spacers exist to provide spacing between sutures, such as those shown in FIGS. 3 and 4, they are not able to prevent entanglement of sutures.

Figure 1:
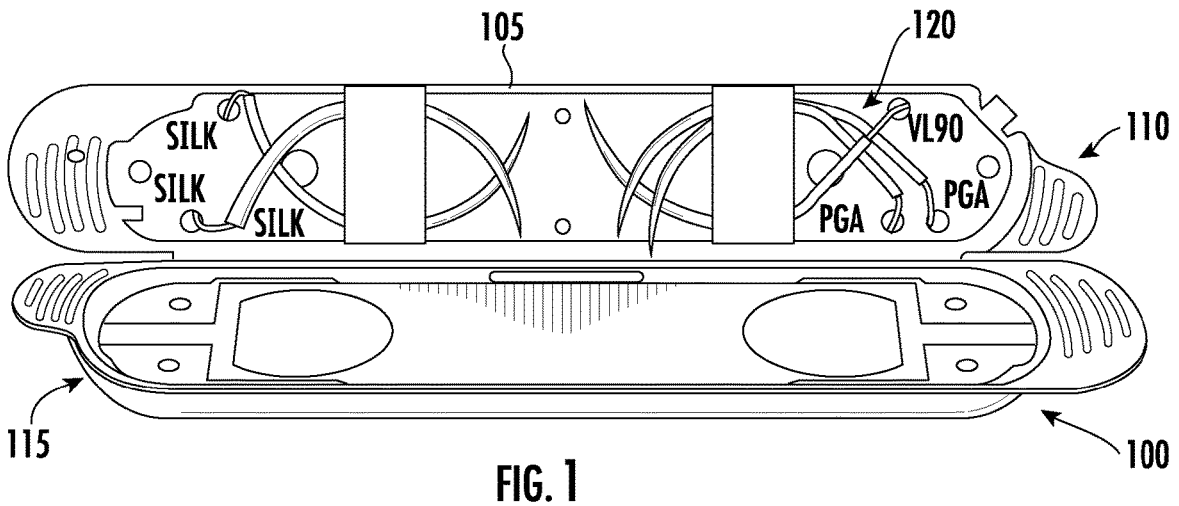
FIG. 1 is a photographic image of a front perspective view of a prototype apparatus for housing surgical instruments according to various embodiments of the present disclosure.

FIG. 1 is a front perspective view of an apparatus for housing surgical instruments according to various embodiments of the present disclosure. Notably, FIG. 1 shows a surgical element carrier 100 dimensioned for insertion through a surgical port during a surgery. The surgical element carrier 100 includes a housing 105, such as a clamshell housing. The housing 105 may include a first housing portion 110 and a second housing portion 115 movable relative to the first housing portion 110, for instance, between a closed position and an open position. The housing 105 may be configured to retain a suture holder base 170 and a plurality of surgical elements 120 therein. In some embodiments, the surgical elements 120 are positioned in the housing 105 in a stacked arrangement such that the surgical elements 120 are accessible when the surgical element carrier is in the open position (e.g., during a surgery).

The surgical elements 120 may include a barbed suture, a silk suture, a 3-0 suture, non-bioabsorbable sutures, such as Polytetrafluoroethylene (PTFE) suture, silk suture; nylon (Ethilon/Monosof [monofilament] and Nurolon/Surgilon [braided]), Polyester fiber (Mersilene/Surgidac [uncoated] and Ethibond/Ti-cron [coated]), Polybutester (Novafil), Coated polybutester (Vascufil), Polypropylene (Prolene), or Surgipro II; and bioabsorbable sutures such as polylactic acid (PLA) or polyglycolic acid (PGA) sutures, Polyglactin 910 (Vicryl), Polycaprolate (Dexon II), Poliglecaprone 25 (Monocryl), Polysorb, Polydioxanone (PDS II), Polytrimethylene carbonate (Maxon), V-Loc 90, V-Loc 180, Quill PDO, or Polyglytone 621 (Caprosyn). The sutures are available in different sizes such as 2-0 through 11-0 and 0 through 7; and different constructions such as monofilament, multifilament/braided, barbed, or barbed such as V-Loc, Quill, or Stratafix.

Figure 5:
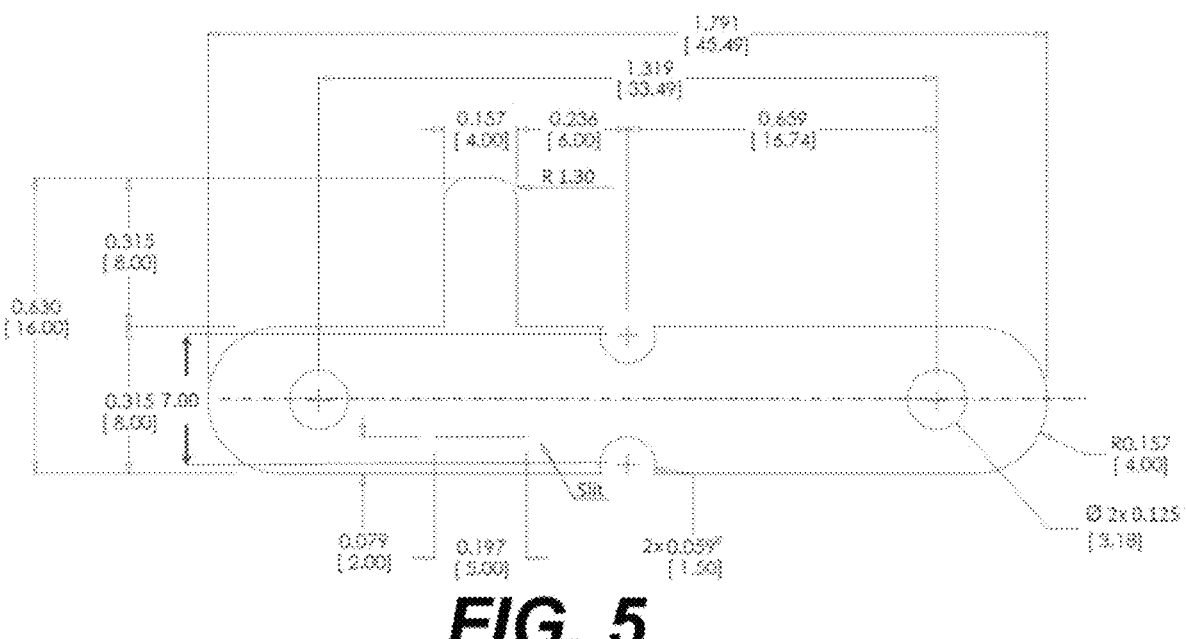
FIG. 5 is a perspective view of a spacer for use in the apparatus of FIG. 1 according to various embodiments of the present disclosure.
Figure 6:
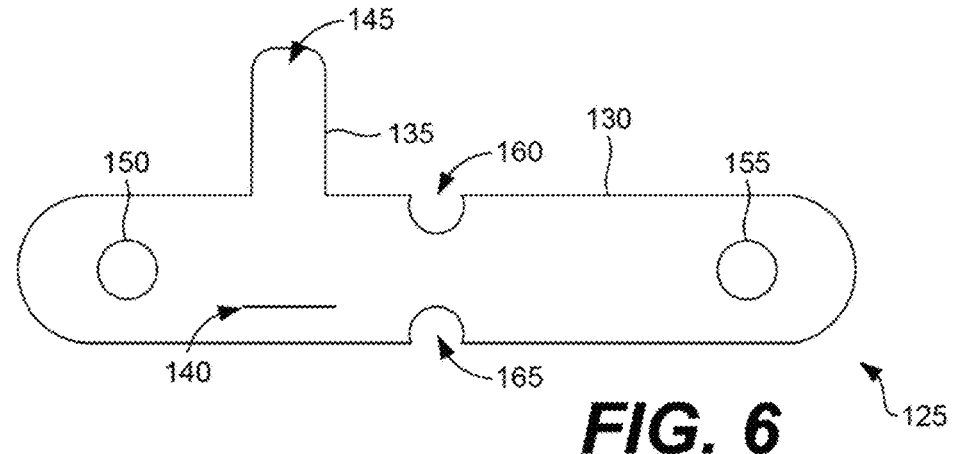
FIG. 6 is a top view of a spacer for use in the apparatus of FIG. 1 according to various embodiments of the present disclosure.
Figure 7:
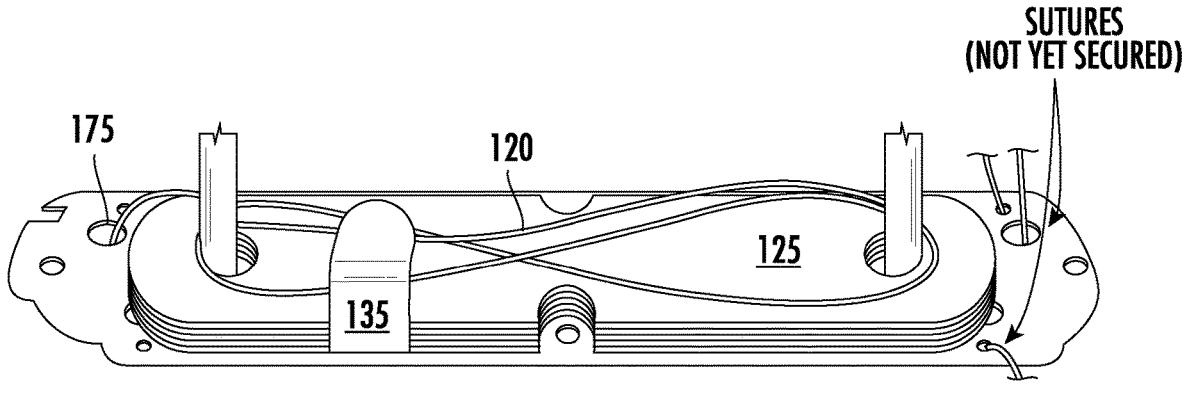
FIGS. 7-8 are photographic images of a perspective views of sutures separated by the spacer of FIGS. 6 and 7 prior to placement in the prototype apparatus of FIG. 1 according to various embodiments of the present disclosure.
Figure 8:
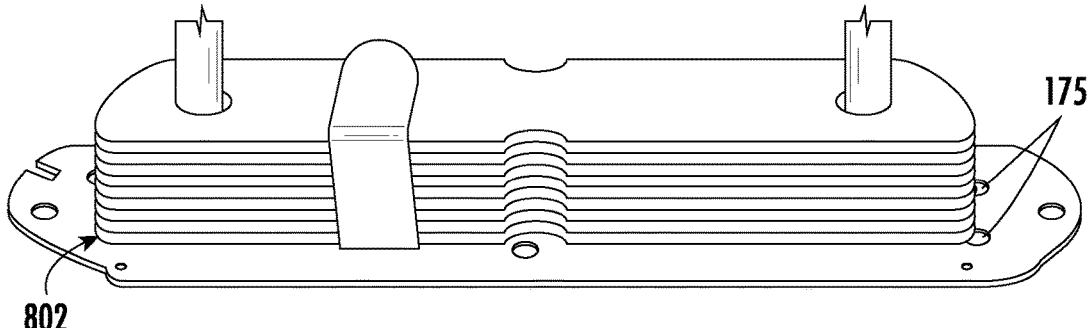

Referring now to FIGS. 5 and 6, in various embodiments, the surgical element carrier 100 may include a spacer 125 having a spacer body 130. The spacer 125 may be positioned between at least two of the surgical elements 120 such that an ideal amount of separation is provided to prevent entanglement of a single surgical element 120 (e.g., a single suture) or entanglement between multiple surgical elements 120 (e.g., multiple sutures). To do so, the spacer 125 and/or the spacer body 130 includes a projecting portion 135 extending from a side of the spacer 125 and/or spacer body 130. As shown in FIGS. 7 and 8, the projecting portion 135 is configured to fold over the spacer body 130 to at least partially overlap one of the surgical elements 120 positioned thereon. As shown, the surgical elements 120 may be stored in a figure-eight configuration.

Referring again to FIGS. 5 and 6, the spacer 125 may further include a slot 140 on a side of the spacer 125 opposite that of the projecting portion 135. The slot 140 may be dimensioned to receive and retain the projecting portion 135 therein. To this end, the slot 140 may have a width substantially similar to a width of the projecting portion 135, thereby forming an interference fit between the slot 140 and the projecting portion 135 when the projecting portion 135 is positioned in the slot 140. The projecting portion 135 may have a distal end 145 for positioning in the slot 140, where the distal end 145 has a convex cross-section. As such, the distal end 145 of the projecting portion 135 may be positioned in the slot 140. In various embodiments, the spacer 125 may be formed of flashspun high-density polyethylene fibers, such as TYVEK® Type 2FS (uncoated) or other suitable medical-grade material. As such, the spacer 125 will be clean and free of dirt, grease, residue, or other foreign matter. The tolerances for manufacturing of the spacer 125 may include: X.X: 0.1 mm, X.XX: 0.01 mm, unless otherwise suited.

In various embodiments, the spacer 125 may further include a first aperture 150 on a first side of the spacer 125 having a circular shape, a second aperture 155 on a second side of the spacer 125 opposite that of the first side having a circular shape, a first notched portion 160 on a third side of the spacer 125 having a semi-circular shape, and a second notched portion 165 on a fourth side of the spacer 125 having a semi-circular shape. Other shapes, however, may be employed.

In some embodiments, small quantity of cut TYVEK® fragments are expected and acceptable. A quantity of cut TYVEK® fragments (hole slugs) may be minimized. Edges of the spacer 125 shall be cut cleanly, and angel-hair or stray fibers shall be minimized. In some embodiments, the spacers

125 may be packaged in bulk format, such that folded or crumpled parts shall be minimized. Additionally, the spacers 125 may be double-bagged.

Figure 2:
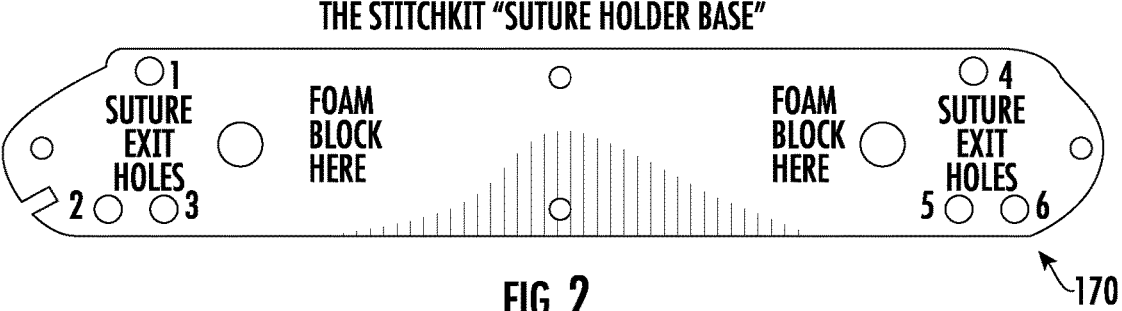
FIG. 2 is a photographic image of a top view of a prototype suture holder base for use in the apparatus of FIG. 1 according to various embodiments of the present disclosure.

Referring to FIG. 2, the surgical element carrier 100 may further include the suture holder base 170 configured to be positioned below a bottom-most one of the surgical elements 120. The suture holder base 170 may include apertures, a first recessed portion, and a second recessed portion, where at least a portion of the plurality of apertures are suture exit holes. Further, as shown in FIG. 1, the suture holder base 170 may include a first foam block 106A positioned in the first recessed portion, and a second foam block 106B positioned in the second recessed portion. The suture holder base 170 may be formed of molded plastic in some embodiments.

The suture side of the surgical element carrier 100 may be designed around the suture holder base 170. The suture holder base 170 is shown in FIG. 1 populated with needles and in FIG. 2 empty, with descriptive labels added. The suture holder base 170 may include, for instance, two foam blocks bonded thereto which may secure needles or other surgical instruments attached to each suture strand. The sutures may be loaded behind the suture holder base 170. As shown, each suture exit hole is labeled to identify the suture type that exits through a respective hole.

Assembling of the surgical element carrier 100 includes, for example, attaching foam to the suture holder base 170 in the locations shown in FIGS. 1 and 2; removing surgical elements 120 (e.g., sutures) from original manufacturer packaging, if needed; and inserting the surgical element (e.g., suture needles) from behind the suture holder base 170 through suture exit holes, and into foam blocks. Once these steps are completed, the suture holder base 170 may be flipped over and placed onto an assembly fixture.

FIG. 7 is a photo of the suture holder base 170 as flipped over. In FIG. 7, surgical elements 120, such as sutures, are shown in the process of being loaded, and each suture is separated from other sutures by layers of spacers 125. Note that each surgical element 120 has TYVEK® both on the top and on bottom thereof. The projecting portion 135, also referred to as a tab, may hold each suture down to its spacer 125, and prevent it from migrating out of its spot. In FIG. 7, suture strands on the right hand side that have not yet been secured into their spacers 125 are shown. On the top-most one of the spacers 125, a violet-colored V-Loc suture 802 can be seen as secured into its spacer 125. On the left side of FIG. 7, the V-Loc strand is shown exiting through exit hole 175.

In each case, surgical elements 120, such as sutures, are sandwiched, by themselves, between layers of spacers 125. They leave the spacer 125 at the ends where they go through their unique exit hole 175, and attach to their needle which is secured in the Foam block on the other side of the suture holder base 170. Through the design, they cannot interact with other sutures.

FIG. 8 shows a photo of the same sub-assembly of FIG. 7 with six sutures loaded. In FIG. 8, surgical elements 120, such as sutures, are shown exiting through unique exit holes 175 on the right. Also, a stack of spacers 125 can be seen with sutures positioned therebetween. Note the needles visible at the bottom, inserted into the foam blocks.

Figure 9:
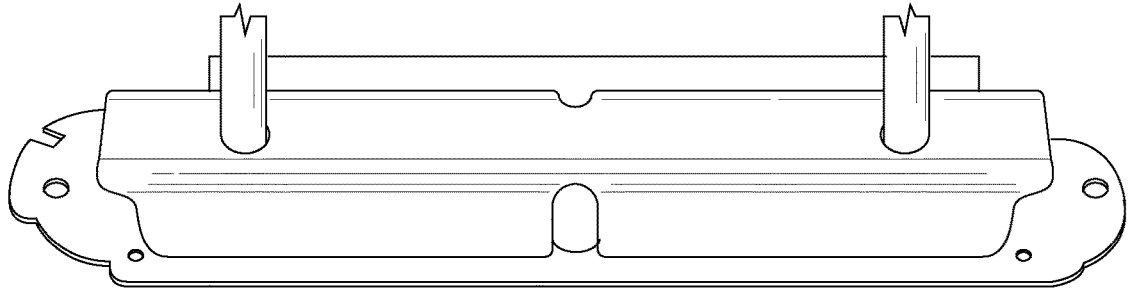
FIGS. 9-10 are photographic images of perspective views of the apparatus of FIG. 1 having sutures separated by the spacer of FIGS. 6 and 7 according to various embodiments of the present disclosure.

FIG. 9 shows the sub-assembly with an inner cover positioned over the suture stack. The inner cover may include a component with the logo printed thereon. In some embodiments, the inner cover is curved, and helps center the surgical element 120 and spacer 125 stack there below. Functionally, the inner cover ensures that the sutures do not poke out of the edges while they are stored or while they are being deployed. Note the needles visible at the bottom, inserted into the foam blocks.

Figure 10:
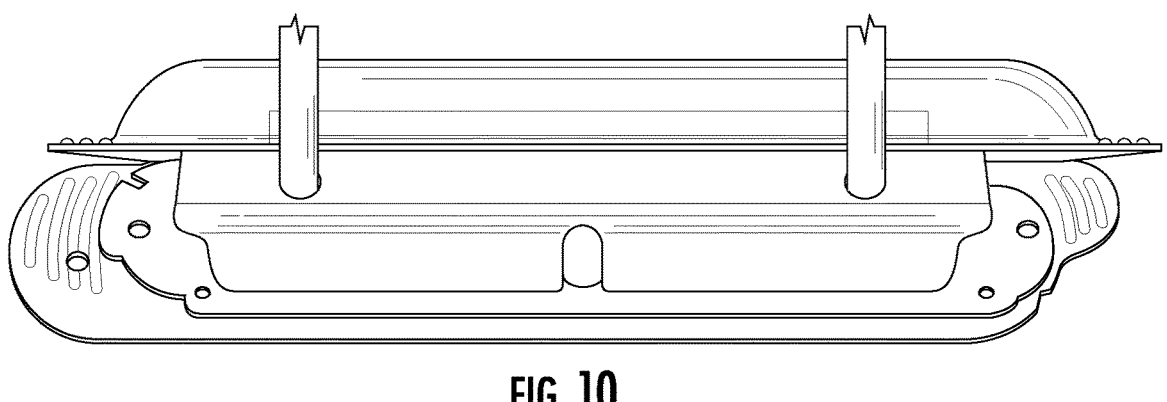
Figure 11:
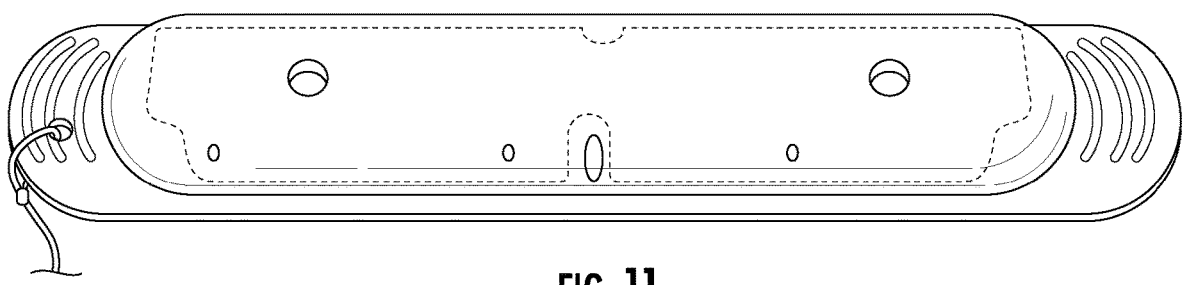
FIG. 11 is a photographic image of a perspective view of an assembled form of the apparatus of FIG. 1 having sutures separated by the spacer of FIGS. 6 and 7 according to various embodiments of the present disclosure.

Turning now to FIG. 10, the figure shows a photo of the sub-assembly with a clear body of a canister applied to the top of the suture stack. At this point the all of the sutures have been loaded into the surgical element carrier 100. Note that the sutures are assembled so that each suture is isolated from all other sutures. They are contained within their own compartment with spacers 125 on top and bottom. The inner cover and the canister body contain them on the sides, and they exit through the suture holder base 170 through unique exit holes 175. Subsequent to the suture loading, the sub-assembly may be removed from a suture loading fixture, the surgical element carrier 100 is flipped over, and the two portions are welded together, for instance, using ultrasonic welding or other suitable affixing medium. The finished form of the surgical element carrier 100 is shown in FIG. 10.

Accordingly, a method of manufacture is described, including forming a first housing portion and a second housing portion; forming a housing dimensioned for insertion through a surgical port used in a surgery by coupling the first housing portion and the second housing portion such that the second housing portion is movable relative to the first housing portion between a closed position and an open position; providing a spacer comprising a projecting portion extending from a side of the spacer; and positioning the spacer positioned between at least two of the plurality of surgical elements inside the housing, the spacer being folded to at least partially overlap one of the plurality of surgical elements positioned thereon.

Additionally, a method is described, including providing a surgical element carrier, comprising: a housing dimensioned for insertion through a surgical port during a surgery, the housing comprising a first housing portion and a second housing portion movable relative to the first housing portion between a closed position and an open position; a plurality of surgical elements in a stacked arrangement within the housing that are accessible when the surgical element carrier is in the open position; and a spacer having a spacer body, the spacer being positioned between at least two of the plurality of surgical elements, the spacer comprising a projecting portion extending from a side of the spacer, the projecting portion being folded over the spacer body to at least partially overlap one of the plurality of surgical elements positioned thereon.

The features, structures, or characteristics described above may be combined in one or more embodiments in any suitable manner, and the features discussed in the various embodiments are interchangeable, if possible. In the following description, numerous specific details are provided in order to fully understand the embodiments of the present disclosure. However, a person skilled in the art will appreciate that the technical solution of the present disclosure may be practiced without one or more of the specific details, or other methods, components, materials, and the like may be employed. In other instances, well-known structures, materials, or operations are not shown or described in detail to avoid obscuring aspects of the present disclosure.

Although the relative terms such as "on," "below," "upper," and "lower" are used in the specification to describe the relative relationship of one component to another component, these terms are used in this specification for convenience only, for example, as a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

In this specification, the terms such as "a," "an," "the," and "said" are used to indicate the presence of one or more elements and components. The terms "comprise," "include," "have," "contain," and their variants are used to be open ended, and are meant to include additional elements, components, etc., in addition to the listed elements, components, etc. unless otherwise specified in the appended claims. The terms "first," "second," etc. are used only as labels, rather than a limitation for a number of the objects.

The above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

Therefore, the following is claimed:

1. A surgical element carrier, comprising:
   a housing dimensioned for insertion through a surgical port during a surgery, the housing comprising a first housing portion and a second housing portion movable relative to the first housing portion between a closed position and an open position;
   a first suture strand,
   a first spacer positioned between the first suture strand and one of the first and second housing portions;
   a second spacer structurally distinct from the first spacer and separated from the first spacer by an intervening gap such that the first suture stand is positioned between the first spacer and the second spacer;
   a second suture strand positioned between the second spacer and one of the first and second housing portions; and
   a suture holder base positioned between the first spacer and the first housing portion of the housing, the suture holding base comprising first and second apertures, wherein the first suture strand extends through the first aperture and the second suture strand extends through the second aperture.

2. The surgical element carrier of claim 1, wherein the suture holder base further comprises:
   a first recessed portion and a second recessed portion;
   a first foam block positioned in the first recessed portion; and
   a second foam block positioned in the second recessed portion.

3. The surgical element carrier of claim 1, wherein the first spacer comprises an elongate main body having a longitudinal axis, first and second opposing end walls and first and second opposing side walls extending continuously between the first and second end walls.

4. The surgical element carrier of claim 3, wherein the second spacer comprises an elongate main body having a longitudinal axis, first and second opposing end walls and first and second opposing side walls extending continuously between the first and second end walls.

5. The surgical element carrier of claim 4, wherein the first and second continuous side walls of the first spacer are spaced from the first and second continuous side walls of the second spacer by the intervening gap.

6. The surgical element carrier of claim 1 wherein the first and second spacers are disposed in a stacked configuration with respect to one another, the first spacer being positioned above the second spacer and spaced apart therefrom by the intervening gap.

7. The surgical element carrier of claim 1, wherein the first spacer comprises a first projecting portion extending from a side of the first spacer, the first projecting portion being folded over at least a portion of the first spacer to at least partially overlap the first suture strand positioned thereon.

8. The surgical element carrier of claim 7, wherein the second spacer comprises a second projecting portion extending from a side of the second spacer, the second projecting portion being folded over at least a portion of the second spacer to at least partially overlap the second suture strand positioned thereon.

* * * * *